(12) United States Patent
Slayton et al.

(10) Patent No.: US 8,074,801 B2
(45) Date of Patent: Dec. 13, 2011

(54) MODULAR PACKAGE FOR FEMININE HYGIENE ARTICLES

(75) Inventors: Nancy Deters Slayton, Springfield, OH (US); Jeanne Marie Hughes, Loveland, OH (US); Virginia Anne Lenahan, Cincinnati, OH (US); David Andrew Dalton, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 36 days.

(21) Appl. No.: 12/414,882

(22) Filed: Mar. 31, 2009

(65) Prior Publication Data
US 2010/0243499 A1 Sep. 30, 2010

(51) Int. Cl.
*B65D 73/00* (2006.01)
(52) U.S. Cl. .................................... 206/440; 206/494
(58) Field of Classification Search ............ 206/440, 206/494, 812, 581, 225, 229, 233; 220/4.27; 229/87.05
See application file for complete search history.

(56) References Cited

U.S. PATENT DOCUMENTS

| | | | | |
|---|---|---|---|---|
| 2,097,185 A * | 10/1937 | Hall | ................................ | 43/54.1 |
| 3,880,342 A | 4/1975 | Longo, Jr. | | |
| 4,082,208 A * | 4/1978 | Lane, Jr. | ........................ | 224/629 |
| 4,139,114 A * | 2/1979 | Long et al. | .................... | 220/23.4 |
| 5,086,926 A * | 2/1992 | Paige et al. | .................... | 206/542 |
| 6,085,908 A * | 7/2000 | Lento | .............................. | 206/581 |
| 6,546,670 B2 * | 4/2003 | Bautner | ............................. | 47/77 |
| 6,708,823 B2 * | 3/2004 | Cottingham et al. | .......... | 206/440 |
| 6,913,146 B2 * | 7/2005 | Bechyne et al. | ............... | 206/440 |
| 7,721,887 B2 * | 5/2010 | Hancock-Cooke et al. | .. | 206/391 |
| 2002/0084203 A1 * | 7/2002 | Cottingham et al. | ......... | 206/440 |
| 2003/0102239 A1 | 6/2003 | Beard | | |
| 2006/0074390 A1 | 4/2006 | Price et al. | | |
| 2006/0142720 A1 | 6/2006 | Zander et al. | | |
| 2006/0283751 A1 * | 12/2006 | Rhea | .............................. | 206/494 |
| 2007/0083178 A1 * | 4/2007 | Nash | ......................... | 604/385.02 |
| 2008/0027403 A1 * | 1/2008 | Hernandez et al. | ....... | 604/385.06 |
| 2008/0264824 A1 * | 10/2008 | Alejandra | ...................... | 206/581 |
| 2010/0244644 A1 * | 9/2010 | Slayton et al. | .............. | 312/348.6 |

FOREIGN PATENT DOCUMENTS

CH 499 429 A 11/1970

(Continued)

OTHER PUBLICATIONS

International Search Report & Written Opinion, PCT/US2010/027743, mailed May 21, 2010, 11 pages.

*Primary Examiner* — Jacob K Ackun
(74) *Attorney, Agent, or Firm* — Andrew J. Hagerty; Amanda T. Barry (57) ABSTRACT

A package having a three dimensional shape and a plurality of modules each being adapted to contain a plurality of feminine hygiene articles. The plurality of modules can include a first end module, a second end module, and one or more middle modules. The first end module and the second end module each can have a free edge and a linked edge, and the one or more middle modules can have a first linked edge and a second linked edge. The linked edge of the first end module can be connected to the first linked edge of a middle module, the one or more middle modules can be connected together at the first and second linked edges, and the linked edge of the second end module can be connected to the second linked edge of a middle module to form a chain of modules. The plurality of modules can be arranged to form the package three dimensional shape.

5 Claims, 4 Drawing Sheets

FOREIGN PATENT DOCUMENTS

| | | | |
|---|---|---|---|
| EP | 0 279 488 A1 | 8/1988 |
| EP | 1 048 576 A1 | 11/2000 |
| FR | 1 388 002 A | 2/1965 |
| FR | 2 050 532 A5 | 4/1971 |
| GB | 2 034 669 A | 6/1980 |
| WO | WO 02/094678 A1 | 11/2002 |

* cited by examiner

MODULAR PACKAGE FOR FEMININE HYGIENE ARTICLES

FIELD OF THE INVENTION

This invention relates to packages having a plurality of modules, and more particularly, to packages having a plurality of modules having one or more feminine hygiene articles disposed therein.

BACKGROUND OF THE INVENTION

Feminine hygiene articles can include absorbent articles, such as, e.g. sanitary napkins, liners, tampons, interlabial products, and incontinence articles, as well as other articles such as, e.g. wipes or powder. These articles are often carried and/or stored by a user in her purse, bag, pocket, or the like. Generally, feminine hygiene articles can be individually wrapped to facilitate ease of carrying and storage. These wrappers tend to degrade, rip, and/or break over time when carried in a purse or bag, however, after which the feminine hygiene article may need to be discarded.

A user may wish to carry multiple feminine hygiene articles in her purse or bag, such as, e.g., an amount sufficient for a day or for several days, such as, e.g., over the course of a menstrual period. In order to accomplish this goal, a user may transfer the desired number of individually wrapped feminine hygiene articles from the retail package into her purse or bag. These articles may become dispersed throughout her purse or bag such that they are difficult to find. In addition, such articles may be easily recognized as feminine hygiene articles, which can be undesirable to a user. As such, some users can carry feminine hygiene articles in discreet cases or pouches that can be reused. These reusable pouches, however, need to be refilled and may become worn or stained after extended use. Alternatively, some users may carry or store multiple feminine hygiene articles in the original retail packaging, which may be too large to facilitate ease of carrying and storage. Trial size retail packages can be purchased, although typically at a premium price, and multiple trial size packages must be purchased and handled to provide sufficient numbers of products for a typical menstrual cycle.

As such, it would be desirable to provide a package for feminine hygiene articles that can provide improved ease of carrying and storage.

SUMMARY OF THE INVENTION

A package having a three dimensional shape and a plurality of modules each being adapted to contain a plurality of feminine hygiene articles is provided. The plurality of modules can include a first end module, a second end module, and one or more middle modules. The first end module and the second end module each can have a free edge and a linked edge, and the one or more middle modules can have a first linked edge and a second linked edge. The linked edge of the first end module can be connected to the first linked edge of a middle module, the one or more middle modules can be connected together at the first and second linked edges, and the linked edge of the second end module can be connected to the second linked edge of a middle module to form a chain of modules. The plurality of modules can be arranged to form the package three dimensional shape.

Also provided is a package having a three dimensional shape and a plurality of modules each being adapted to contain a plurality of feminine hygiene articles. The plurality of modules can include a first end module, a second end module, and one or more middle modules. The first end module and the second end module each can have a free edge and a linked edge, and the one or more middle modules can have a first linked edge and a second linked edge. The linked edge of the first end module can be connected to the first linked edge of a middle module along a line of weakness that is separable, the one or more middle modules can be connected together at the first and second linked edges along lines of weakness that are separable, and the second linked edge of the middle module can be connected to the linked edge of the second end module along a line of weakness that is separable. The plurality of modules can form a chain that can be adapted to fold to form the package three dimensional shape.

Also provided is a package comprising a three dimensional shape that is a prism. The package includes a plurality of modules each having a three dimensional shape that is a prism and each being adapted to contain a plurality of feminine hygiene articles. The plurality of modules can comprise a first end module, a second end module, and one or more middle modules. The first end module and the second end module each can have a free edge and a linked edge, and the one or more middle modules can have a first linked edge and a second linked edge. The linked edge of the first end module can be connected to the first linked edge of a middle module, the one or more middle modules can be connected together at the first and second linked edges, and the linked edge of the second end module can be connected to the second linked edge of a middle module to form a chain of modules. The plurality of modules can be arranged to form the package three dimensional shape.

DETAILED DESCRIPTION OF THE INVENTION

The present invention relates to packages having a plurality of modules. Each module can have one or more feminine hygiene articles disposed therein. In certain embodiments, the plurality of modules can include a pair of end modules and one or more middle modules that can be connected together to form a chain of modules. In addition, in certain embodiments, each module can be a shape and the plurality of modules can be arranged together to form a second shape.

Such packages can promote ease of carrying, storage, and use by allowing a user to detach modules as needed. Because the feminine hygiene articles are contained within the module, they can be retained together in a bag, a purse, or other container. The module can also provide protection from damage. A module can include a suitable number of feminine hygiene articles, such as, e.g., an amount that could typically be used in a day, several days, or more. In certain embodiments, different types or sizes of feminine hygiene articles can be included in different modules of a package so that a user can select and detach the appropriate module as necessary.

As used herein, the term "feminine hygiene article" refers to articles such as, e.g., disposable absorbent articles that can be worn by women for menstrual and/or light incontinence control, such as, for example, sanitary napkins, tampons, interlabial products, incontinence articles, and liners. As used herein, the term "feminine hygiene article" can also refer to other articles for use in the pudendal region such as, e.g., wipes and/or powder. As used herein, a feminine hygiene article can include any associated wrapping or applicator that typically can be associated with the feminine hygiene article. For example, a feminine hygiene article can be a tampon that may or may not include an applicator and/or can be a sanitary napkin that may or may not include a wrapper, such as, e.g. a wrapper that individually encloses the sanitary napkin.

As used herein, the term "absorbent article" refers to devices that absorb and/or contain a substance, such as, e.g., body exudates. A typical absorbent article can be placed against or in proximity to the body of the wearer to absorb and contain various body exudates.

As used herein, the term "tampon" refers to any type of absorbent structure such as, e.g., an absorbent mass, that can be inserted into the vaginal canal or other body cavity for the purpose of, such as, e.g. absorbing fluid therefrom, aiding in wound healing, and/or for delivering materials, such as moisture or active materials such as medicaments. The term "tampon" can also include the combination of an absorbent structure with any type of applicator that can be associated with the absorbent structure to facilitate insertion of a tampon into the vaginal canal or other body cavity. In certain embodiments, the term "tampon" can also include a wrapper that can individually package the tampon and/or the tampon in combination with an applicator.

As used herein, the term "shape" refers to a geometric shape having at least one axis of symmetry. For example, in certain embodiments, a shape can be a polygon, such as, e.g., a triangle, a square, a rectangle, a parallelogram, a rhombus, a trapezoid, a pentagon, a hexagon, a heptagon, or an octagon, or can be a circle, an oval, an ellipse, or any other suitable geometric shape. In certain embodiments, a shape can be "regular," such as, e.g., wherein all sides are equal and all angles are equal.

As used herein, the term "three dimensional shape" refers to shapes with a width, a height, and a depth. For example, in certain embodiments, a three dimensional shape can be a cube, a sphere, a cylinder, a prism, a cone, a pyramid, or a polyhedron. A three dimensional shape can have a cross-section that is a shape. For example, in certain embodiments, the three dimensional shape can be a cylinder having a cross-section and two parallel bases that are a circle. Alternatively, the three dimensional shape can be a prism having a cross-section and two parallel bases that are a polygon, such as, e.g., a triangle, a square, a hexagon, a pentagon, or an octagon. In certain embodiments, a three dimensional shape can be defined by its cross-section and its shape, such as, e.g., a triangular prism, a hexagonal prism, an octagonal prism, a circular cylinder, an elliptical cylinder, or the like.

As used herein, the term "line of weakness" refers to a plurality of weakness points arranged in a row. The row can be straight, bent, angled, curved, and/or can change direction. In certain embodiments, one or more of the individual weakness points can overlap to form the line of weakness. In addition, or alternatively, one or more of the individual weakness points can be spaced apart from one another to form the line of weakness. The one or more lines of weakness can be formed by perforations or by depressions. A line of weakness can be formed in any suitable manner, such as, e.g., mechanically and/or thermally, such as, for example, by using a laser and/or chemically.

Figure 1:
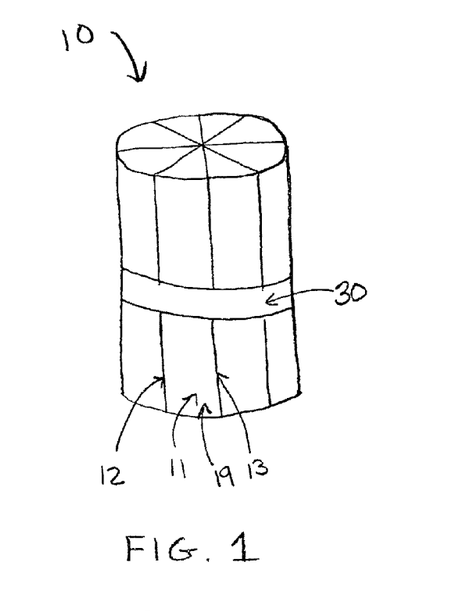
FIG. 1 is a perspective view of one embodiment of the invention.

FIG. 1 shows an example of a modular package 10. Modular package 10 includes a plurality of modules 11. Each module 11 has a first side 12 and a second side 13. Each module 11 can be adapted to contain a plurality of feminine hygiene articles. As shown in FIG. 1, each module can have a three dimensional shape, such as, e.g., a triangular prism, that can have a cross-section that is a shape, such as, e.g., a triangle. In certain embodiments, the modules 11 can be folded into modular package 10 having a three dimensional shape, such as, e.g., a circular cylinder, that can have a cross-section that is a shape, such as, e.g., a circle. In addition, the modules 11 can be contained in place to form modular package 10 by one or more fastening devices 30.

Figure 2:
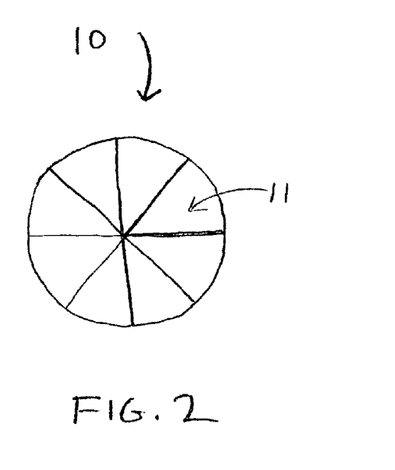
FIG. 2 is an end view of one embodiment of the invention.

FIG. 2 shows an example of a modular package 10 that includes a plurality of modules 11.

Figure 3:
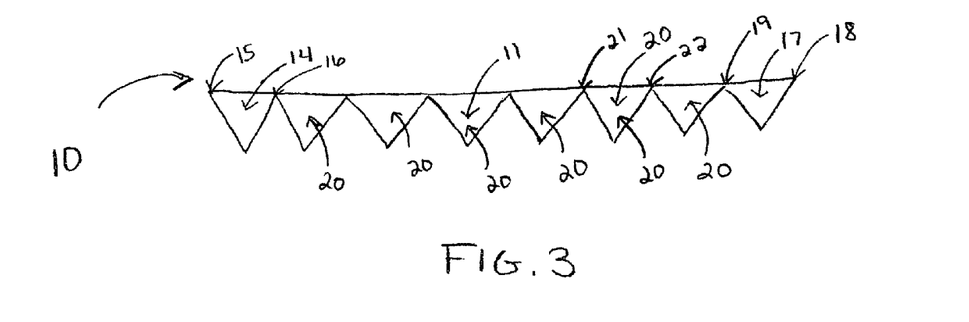
FIG. 3 is a top view of one embodiment of the invention.

As shown in FIG. 3, in certain embodiments, the plurality of modules 11 can include a first end module 14 that can include a free edge 15 and a linked edge 16 and a second end module 17 that can include a free edge 18 and a linked edge 19. In addition, the plurality of modules 11 can include one or more middle modules 20 that can include a first linked edge 21 and a second linked edge 22. As shown in FIG. 3, the plurality of modules 11 can be arranged to form a linked chain of modules. For example, in certain embodiments, the linked edge 16 of the first end module 14 can be connected to the first linked edge 21 of the middle module 20 and the second linked edge 22 of the middle module 20 can be connected to the first linked edge 21 of another middle module 20 or can be connected to the linked edge 19 of the second end module 17. As shown in FIG. 3, the free edge 15 of the first end module 14 and the free edge 18 of the second end module 17 are free of connections to any other module 11 when the modular package 10 is in an unfolded configuration. In certain embodiments, when the modules 11 are formed into modular package 10, such as, e.g., by folding, free edge 15 of the first end module 14 and free edge 18 of the second end module 17 can be brought together and held, such as, e.g., by one or more fastening devices 30.

Figure 4:
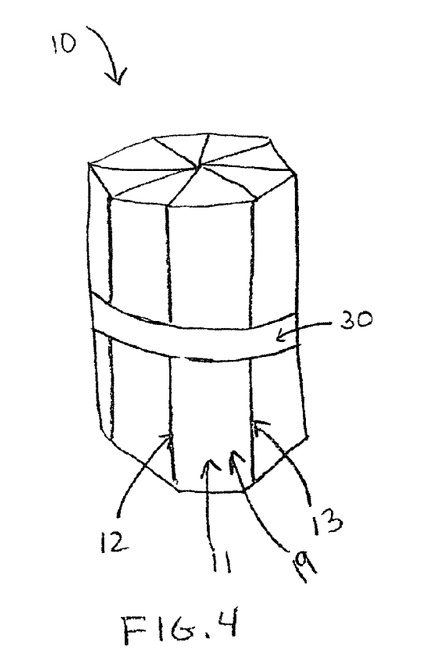
FIG. 4 is a perspective view of one embodiment of the invention.

FIG. 4 shows an example of a modular package 10. Modular package 10 includes a plurality of modules 11. Each module 11 has a first side 12 and a second side 13. Each module 11 can be adapted to contain a plurality of feminine hygiene articles. As shown in FIG. 4, each module can have a three dimensional shape, such as, e.g., a triangular prism, that can have a cross-section that is a shape, such as, e.g., a triangle. In certain embodiments, the modules 11 can be folded into modular package 10 having a three dimensional shape, such as, e.g., a octagonal prism, that can have a cross-section that is a shape, such as, e.g., a octagon. In addition, the modules 11 can be contained in place to form modular package 10 by one or more fastening devices 30.

Figure 5:
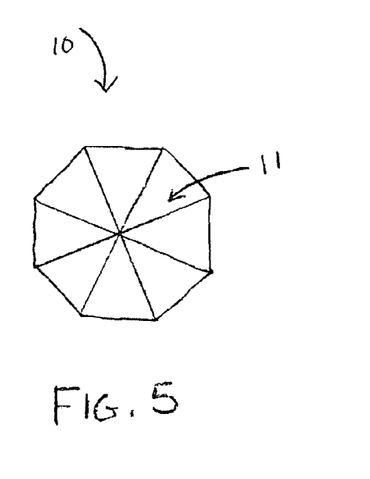
FIG. 5 is an end view of one embodiment of the invention.

FIG. 5 shows an example of a modular package 10 that includes a plurality of modules 11.

Figure 6:
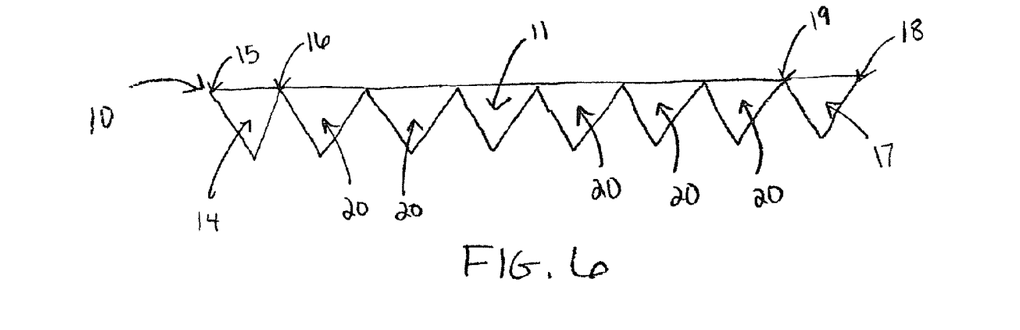
FIG. 6 is a top view of one embodiment of the invention.

As shown in FIG. 6, in certain embodiments, the plurality of modules 11 can include a first end module 14 that can include a free edge 15 and a linked edge 16 and a second end module 17 that can include a free edge 18 and a linked edge 19. In addition, the plurality of modules 11 can include one or more middle modules 20 that can include a first linked edge 21 and a second linked edge 22. As shown in FIG. 6, the plurality of modules 11 can be arranged to form a linked chain of modules. For example, in certain embodiments, the linked edge 16 of the first end module 14 can be connected to the first linked edge 21 of the middle module 20 and the second linked edge 22 of the middle module 20 can be connected to the first linked edge 21 of another middle module 20 or can be connected to the linked edge 19 of the second end module 17. As shown in FIG. 6, the free edge 15 of the first end module 14 and the free edge 18 of the second end module 17 are free of connections to any other module 11 when the modular package 10 is in an unfolded configuration. In certain embodiments, when the modules 11 are formed into modular package 10, such as, e.g., by folding, free edge 15 of the first end module 14 and free edge 18 of the second end module 17 can be brought together and held, such as, e.g., by one or more fastening devices 30.

Figure 7:
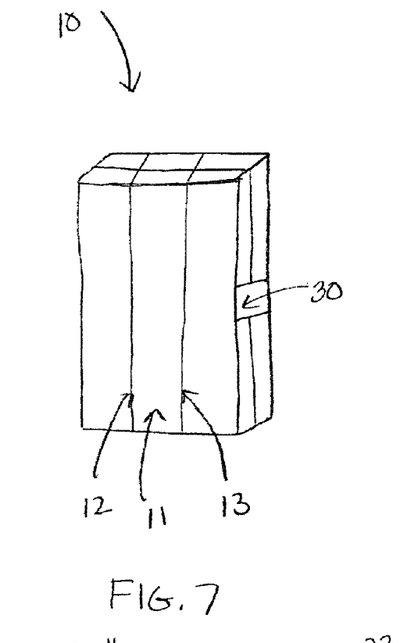
FIG. 7 is a perspective view of one embodiment of the invention.

FIG. 7 shows an example of a modular package 10. Modular package 10 includes a plurality of modules 11. Each module 11 has a first side 12 and a second side 13. Each module 11 can be adapted to contain a plurality of feminine hygiene articles. As shown in FIG. 7, each module can have a three dimensional shape, such as, e.g., a rectangular prism, that can have a cross-section that is a shape, such as, e.g., a rectangle. In certain embodiments, the modules 11 can be folded into modular package 10 having a three dimensional shape, such as, e.g., a rectangular prism, that can have a cross-section that is a shape, such as, e.g., a rectangle. In addition, the modules 11 can be contained in place to form modular package 10 by one or more fastening devices 30.

Figure 8:
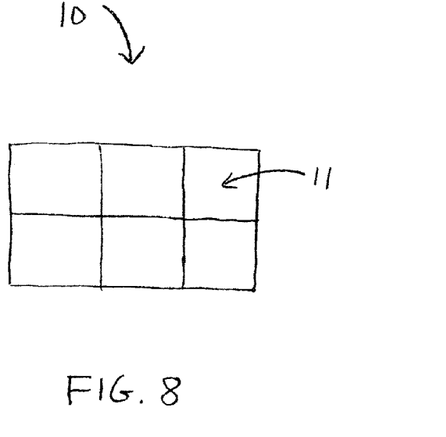
FIG. 8 is an end view of one embodiment of the invention.

FIG. 8 shows an example of a modular package 10 that includes a plurality of modules 11.

Figure 9:
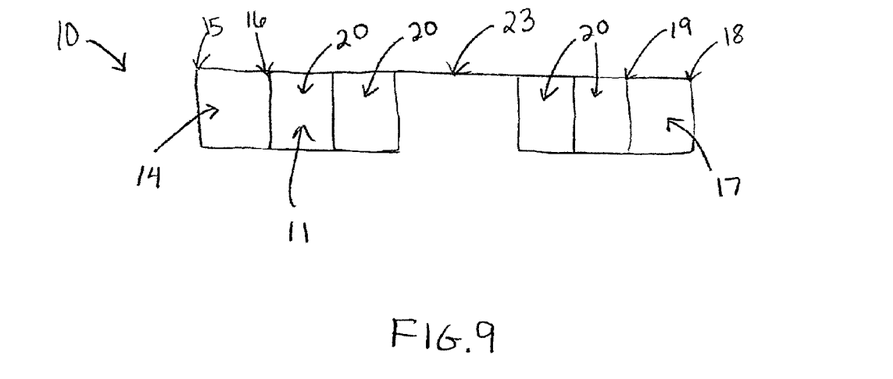
FIG. 9 is a top view of one embodiment of the invention.

As shown in FIG. 9, in certain embodiments, the plurality of modules 11 can include a first end module 14 that can include a free edge 15 and a linked edge 16 and a second end module 17 that can include a free edge 18 and a linked edge 19. In addition, the plurality of modules 11 can include one or more middle modules 20 that can include a first linked edge 21 and a second linked edge 22. As shown in FIG. 9, the plurality of modules 11 can be arranged to form a linked chain of modules. For example, in certain embodiments, the linked edge 16 of the first end module 14 can be connected to the first linked edge 21 of the middle module 20 and the second linked edge 22 of the middle module 20 can be connected to the first linked edge 21 of another middle module 20 or can be connected to the linked edge 19 of the second end module 17. As shown in FIG. 9, the free edge 15 of the first end module 14 and the free edge 18 of the second end module 17 are free of connections to any other module 11 when the modular package 10 is in an unfolded configuration. In addition, in certain embodiments, the package 10 can include a bridge 23 that can connect one or more modules 11. In certain embodiments, when the modules 11 are formed into modular package 10, such as, e.g., by folding, free edge 15 of the first end module 14 and free edge 18 of the second end module 17 can be brought together and held, such as, e.g., by one or more fastening devices 30.

Figure 10:
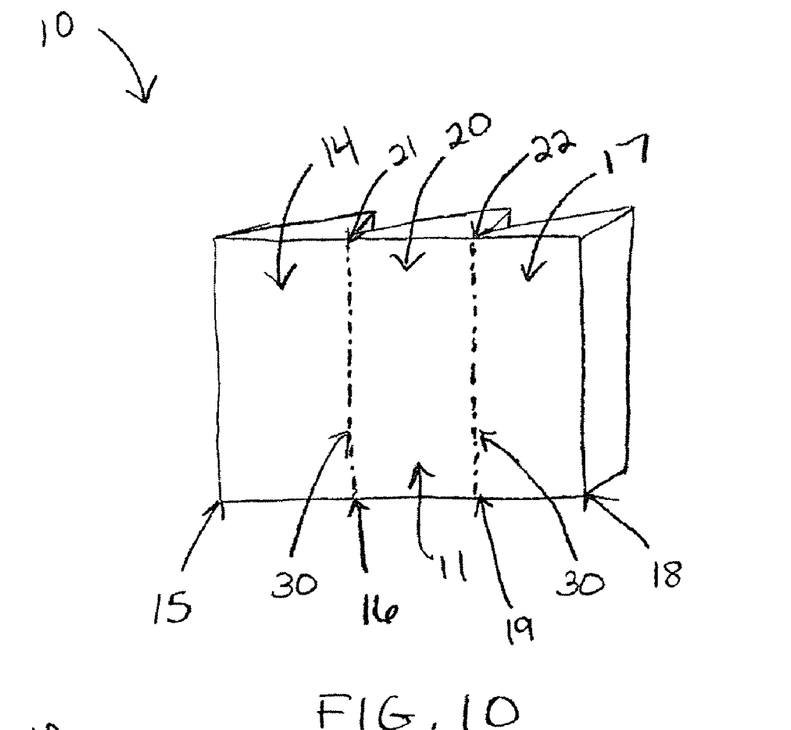
FIG. 10 is a perspective view of one embodiment of the invention.

FIG. 10 shows an example of a modular package 10. Modular package 10 includes a plurality of modules 11. Each module 11 has a first side 12 and a second side 13. Modular package 10 can include a first end module 14 that can include a free edge 15 and a linked edge 16 and a second end module 17 that can include a free edge 18 and a linked edge 19. In addition, the plurality of modules 11 can include one or more middle modules 20 that can include a first linked edge 21 and a second linked edge 22. As shown in FIG. 10, the plurality of modules 11 can be arranged to form a linked chain of modules. For example, in certain embodiments, the linked edge 16 of the first end module 14 can be connected to the first linked edge 21 of the middle module 20 and the second linked edge 22 of the middle module 20 can be connected to the linked edge 19 of the second end module 17. As shown in FIG. 10, each module 11 can be integrally joined to the adjacent module 11 by a frangible connection, such as, e.g., line of weakness 30.

Figure 11:
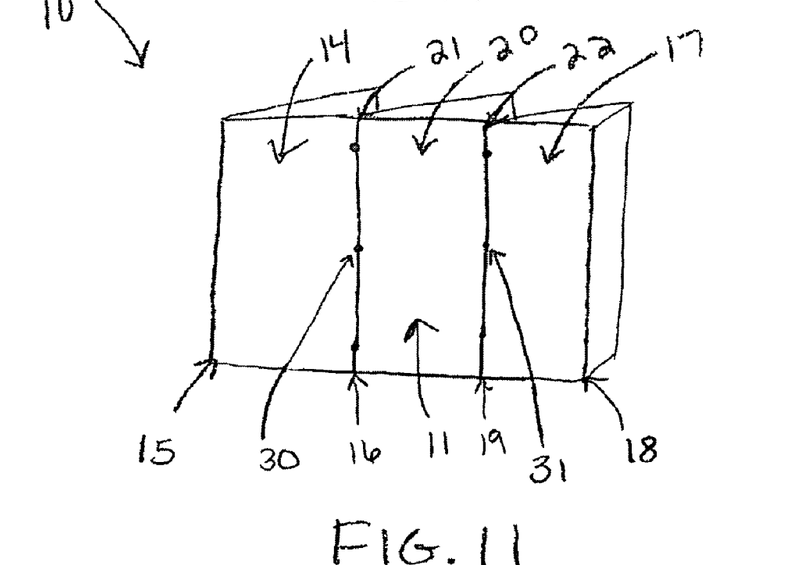
FIG. 11 is a perspective view of one embodiment of the invention.

FIG. 11 shows an example of a modular package 10 that includes a plurality of modules 11. Each module 11 has a first side 12 and a second side 13. Modular package 10 can include a first end module 14 that can include a free edge 15 and a linked edge 16 and a second end module 17 that can include a free edge 18 and a linked edge 19. In addition, the plurality of modules 11 can include one or more middle modules 20 that can include a first linked edge 21 and a second linked edge 22. As shown in FIG. 11, the plurality of modules 11 can be arranged to form a linked chain of modules. For example, in certain embodiments, the linked edge 16 of the first end module 14 can be connected to the first linked edge 21 of the middle module 20 and the second linked edge 22 of the middle module 20 can be connected to the linked edge 19 of the second end module 17. As shown in FIG. 11, each module 11 can be integrally joined to the adjacent module 11 by a frangible connection, such as, e.g., one or more joints 31.

As exemplified above, the modules are joined together, such as, e.g., to form a chain. In certain embodiments, the modules can be integrally joined in any suitable manner, such as, e.g., by forming the modules as a contiguous set, by connecting the modules together, such as, e.g., using adhesive or other mechanical means, or in any other suitable way. In certain embodiments, the modules are separable from one another, such as, e.g., by breaking a frangible connection, such as, e.g., along a line of weakness provided between the modules, or any another suitable way. In addition, in certain embodiments, the modules can be joined together by attaching the modules in a suitable arrangement, such as, e.g., side by side, in a row, or other suitable arrangement, to a fastening device, such as, e.g., a strip, sheet, ribbon, tie, or other suitable device.

The package can be any shape suitable for containing one or more feminine hygiene articles. In certain embodiments, the package can have a three dimensional shape that can have a width, a height, and a depth, such as, e.g., a cube, a sphere, a cylinder, a prism, a cone, a pyramid, or a polyhedron, or any other suitable shape. In addition, the package can have a cross-section that is a shape, such as, e.g., a polygon, such as, e.g., a triangle, a square, a rectangle, a parallelogram, a rhombus, a trapezoid, a pentagon, a hexagon, a heptagon, an octagon, a circle, an oval, an ellipse, or any other suitable geometric shape. In certain embodiments, the package can have a three dimensional shape that can be formed from a plurality of modules having a three dimensional shape. For example, in certain embodiments, the package can have a three dimensional shape such as, e.g., a circular cylinder or an octagonal prism, that can be formed from a plurality of modules having a three dimensional shape that is a triangular prism, or a three dimensional shape such as, e.g., a rectangular prism or a square prism, that can be formed from a plurality of modules having a three dimensional shape that is a square prism, a rectangular prism, and/or a triangular prism.

The package includes a plurality of modules, each adapted to contain one or more feminine hygiene articles. The package can include any suitable number of modules, such as, e.g., at least two, at least three, at least four, at least five, at least six, at least seven, at least eight, or any other suitable number. In certain embodiments, the package can include a plurality of modules each containing the same size and/or type of feminine hygiene articles. Alternatively, the package can include a plurality of modules each containing different size and/or type of feminine hygiene articles, such as, e.g., a package having one or more modules containing lite tampons, one or more modules containing regular tampons, and one or more modules containing super tampons, or a package having one or more modules containing tampons and one or more modules containing sanitary napkins, or any other suitable arrangement. In certain embodiments, each module can contain one or more kits, such as, e.g., a tampon, a liner, and a wipe. The modules in a package can have the same number and/or configuration of sizes and/or types of feminine hygiene articles or the modules can have a different number and/or configuration of sizes and/or types of feminine hygiene articles.

Modules can have any shape suitable for containing one or more feminine hygiene articles. In certain embodiments, the module can have a three dimensional shape that can have a width, a height, and a depth, such as, e.g., a cube, a sphere, a cylinder, a prism, a cone, a pyramid, or a polyhedron, or any other suitable shape. In addition, the module can have a cross-section that is a shape, such as, e.g., a polygon, such as, e.g., a triangle, a square, a rectangle, a parallelogram, a rhombus, a trapezoid, a pentagon, a hexagon, a heptagon, an octagon, a circle, an oval, an ellipse, or any other suitable geometric shape. In certain embodiments, each module in a package can be the same shape. Alternatively, the modules in a package can be different shapes. In certain embodiments, modules can have different shapes for different types and/or sizes of feminine hygiene articles.

The module three dimensional shape and the package three dimensional shape can be the same or different. For example, in certain embodiments, the modules and the package can be different shapes, such as, e.g., when both the modules and the package can be considered prisms, but can have different cross-sectional shapes, such as, e.g., modules that are a triangular prisms forming a packaging that is a octagonal prism. Alternatively, the modules and the package can be the same shape, such as, e.g., when both the modules and the package can be considered rectangular prisms.

In certain embodiments, each module can substantially enclose one or more feminine hygiene articles. For example, in certain embodiments, each module can completely enclose one or more feminine hygiene articles. Any suitable number of feminine hygiene articles can be enclosed within the module, such as, e.g., one, two, three, four, five, six, seven, eight, nine, ten, or more, or any other suitable number. In certain embodiments, each module can enclose a plurality of feminine hygiene articles, such as, e.g., two or more feminine hygiene articles, such as, e.g., three or more, four or more, five or more, or six or more feminine hygiene articles.

In certain embodiments, the module can include an opening device. For example, in certain embodiments, the module can include a flap, a tab, or other suitable device for assisting a user in opening the module. In addition, or alternatively, the module can include one or more lines of weakness that can be separated to provide access to the interior of the module. In certain embodiments, the module can include a closure, such as, e.g., a resealable closure that can function, for example, to close the module after a feminine hygiene article is removed.

The plurality of modules can be arranged to form the package in any suitable manner. For example, in certain embodiments, the plurality of modules can be folded together to form the package. The plurality of modules can be folded, stacked, or arranged in any manner suitable for forming the package.

In certain embodiments, the package can include a fastening device, such as, e.g., a ribbon, a tape, a tab, wrapping, or any other fastening device suitable for holding the plurality of modules in the package form.

The package can be made of any suitable material. In certain embodiments, the package can comprise one or more inflexible materials, such as, for example, cardboard, paperboard, cartonboard, chipboard, plywood, SBS, metal, plastic, paper, card stock, fabric, ceramic, polymer, natural or synthetic fibers, webs, mesh, screen, wood, composite, mixtures or combinations thereof, or any other suitable material. In certain embodiments, inflexible materials can be preferred to provide modules and a package having the desired three dimensional shapes. Alternatively, or in addition, the package can be made of a flexible material, such as, e.g., blown or cast film in a blend of low density polyethylene and linear low density polyethylene, metallocenes, ethylene vinyl acetate, surlyn, polyethylene terephthalate, biaxally oriented polypropylene, nylon, combinations thereof, or any other material. In certain embodiments the package can be disposable, such as, e.g., not intended for reuse.

Any suitable feminine hygiene article and/or combination of feminine hygiene articles can be disposed in the package. Suitable feminine hygiene articles include, e.g., absorbent articles, such as, e.g., tampons, sanitary napkins, pantiliners, incontinence articles, and/or interlabial pads, and other articles such as, e.g. wipes and/or powder. In certain embodiments, individual feminine hygiene articles can be individually wrapped before enclosure in the module.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package comprising a three dimensional shape and a plurality of modules being adapted to contain a plurality of feminine hygiene articles, the plurality of modules comprising
   a first end module,
   a second end module, and
   at least one middle module disposed between the first and second end modules,
     wherein the plurality of modules are connected together by a module linked edge,
     wherein one of the plurality of modules contains a tampon of a first size, wherein another of the plurality of modules contains a tampon of a second size that is different than the first size, and wherein another of the plurality of modules contains a feminine hygiene article other than a tampon selected from the group consisting of a liner and a sanitary napkin.

2. The package of claim 1, wherein the plurality of modules comprise a three dimensional shape.

3. The package of claim 2, wherein the three dimensional shape of the modules is different from the three dimensional shape of the package.

4. The package of claim 1, wherein the plurality of modules each comprise a resealable opening.

5. The package of claim 1, wherein the modules are formed from paper, cardboard, paperboard, cartonboard, or combinations thereof.

* * * * *